(12) United States Patent
Kocher (10) Patent No.: US 10,490,305 B1
(45) Date of Patent: Nov. 26, 2019

(54) MOBILE MEDICAL IDENTIFICATION AND WARNING SYSTEM

(71) Applicant: Robert Kocher, McLean, VA (US)

(72) Inventor: Robert Kocher, McLean, VA (US)

( * ) Notice: Subject to any disclaimer, the term of this patent is extended or adjusted under 35 U.S.C. 154(b) by 163 days.

(21) Appl. No.: 15/732,706

(22) Filed: Dec. 19, 2017

Related U.S. Application Data (60) Provisional application No. 62/498,247, filed on Dec. 20, 2016.

(51) Int. Cl.
| | |
|---|---|
| *G16H 10/65* | (2018.01) |
| *G06K 9/00* | (2006.01) |
| *G06K 9/22* | (2006.01) |
| *G16H 40/67* | (2018.01) |

(52) U.S. Cl.
CPC ......... *G16H 10/65* (2018.01); *G06K 9/00087* (2013.01); *G06K 9/00288* (2013.01); *G06K 9/00617* (2013.01); *G06K 9/00892* (2013.01); *G06K 9/22* (2013.01); *G16H 40/67* (2018.01)

(58) Field of Classification Search
CPC ........ G16H 10/60; G16H 10/65; G16H 40/67; G06K 9/00087; G06K 9/00288; G06K 9/00617; G06K 9/00892; G06K 9/22; G06K 19/06028; G06K 19/06037; G06K 2019/06028; G06K 2019/06037; G06K 2019/06234; G06K 2019/06253; G07C 9/00071
USPC ........................................................ 382/116
See application file for complete search history.

(56) References Cited

U.S. PATENT DOCUMENTS

| | | | | |
|---|---|---|---|---|
| 4,557,693 | A * | 12/1985 | Elggren | A61B 5/1178 283/70 |
| 2006/0015368 | A1* | 1/2006 | Hockey | G16H 10/65 705/2 |
| 2013/0035581 | A1* | 2/2013 | Vesto | G16H 10/60 600/407 |
| 2013/0179185 | A1* | 7/2013 | Duffy | G06Q 10/10 705/3 |
| 2013/0197941 | A1* | 8/2013 | Cochran | G06Q 50/22 705/3 |
| 2015/0039341 | A1* | 2/2015 | Markman | G16H 10/60 705/3 |
| 2015/0213207 | A1* | 7/2015 | Amarasingham | G06N 5/04 705/2 |

* cited by examiner

*Primary Examiner* — Ali Bayat (57) ABSTRACT

A mobile System is disclosed that uses biometric identification to identify an injured person, provides an immediate warning of a special or medical condition, and can transmit that data to the hospital along with additional photos and video of the injury. This provides emergency rooms with access to the patient's medical records, history of the patient's medical conditions, real-time photographs which better prepare the medical staff to identify the incoming patent prior to the patient arriving at the hospital. Additional embodiments involve Law Enforcement uses where criminal, missing persons and wanted persons' data are used for identification. Military uses involve the use of data of military persons of concern. Medical fraud prevention documents medical transport, patient identity, verification of medical cards; and physician services documentation. This invention can save the medical services community billions of dollars and prevent administrative mistakes which can result in injury and/or loss of life.

20 Claims, 5 Drawing Sheets

MOBILE MEDICAL IDENTIFICATION AND WARNING SYSTEM

CROSS-REFERENCE TO RELATED APPLICATION

This application claims priority from U.S. Provisional Application No. 62/498,247 filed on Dec. 20, 2016.

BACKGROUND

Field of the Invention

This invention relates to the capture by first responders, of biometric data; such as face, fingerprint or iris; and injury data such as photographs and/or video pertaining to injured person(s), with the purpose of utilizing biometric data for identity linkage to medical records and video/photographs; in order to better enable first responders/medical personnel make better informed and highly effective medical decisions regarding the injured person(s) in question. The invention also related to preventing medical fraud and providing military and law enforcement identification of dangerous individuals.

Description of the Related Art

When first responders, ambulance drivers, policemen, etc., arrive on the scene of an accident or injury, they call for emergency vehicles to evacuate the injured individuals for treatment. The first responders will generally look in wallets and purses to determine the identity or anything related to the injured individual. In many situations, identification documents are not located or can be confused with other injured persons or victims. Current state of the art processes are not focused on identity; but rather are focused on the immediate injury. The injured person(s) are transported to hospitals with, in many cases, unknown identity. When injured persons are brought in to emergency rooms, the treatment may begin without knowing the identity of the injured person(s), and in some cases the injured person is unconscious in an intense or critical condition whereby they are unable to communicate their identity. As a result, hospital personnel don't immediately determine whether the injured individual has any allergies or special medical conditions.

The linkage of a person to their medical record is currently based on the name, date of birth and potentially the injured person's Social Security number (SSN). However, even in these situations, a problem may develop with multiple medical records directed to the same individual because a new record is created when the person is brought to the hospital or emergency room. This results in an incomplete and inaccurate medical record. Consolidating these medical files is costly and raises the issue of inaccuracy. Another problem with the current state of the art centers on medical fraud. The first area of fraud involves a patient with someone else's medical card. This occurs when the injured person does not have insurance and either takes someone's card or borrows a family member's card with permission. It's believed that 50% of patient medical fraud comes from stolen cards and 50% are from borrowed cards. This causes a serious situation where the wrong medical record is linked to the card. Normally, a hospital requires a driver license and a medical card. Nevertheless, the very small photo on the driver license may not be sufficient for the hospital administrative personnel to effectively identity the injured person(s). The hospital administrative personnel check the injured person's medical identification card and the driver's license. When the name on the medical identification card and the driver's license match, the hospital administrative personnel will ask for the injured person(s) date of birth (DOB); and the injured person(s) is then admitted into the hospital.

Another example of medical fraud concerns ambulance or other medical transportation services. There are numerous fraud cases where by the ambulance transportation service claims they performed a higher number of transportation services than were actually performed. An example would be a medical transportation service claiming eight runs a day when in reality they only performed three runs per day. Medical transportation service organizations basically submit names saying who they took to the hospital and that is generally sufficient for payment. Transportation services are normally paid by the hospital, county or state.

Still another area of medical fraud is when the doctor claims they saw a patient or numbers of patients that in reality weren't seen or treated. Identification of the patient, verification of the medical record relating to the patient and verification of medical services performed are areas that are dangerous to the patient and areas of potential fraud.

It would be beneficial to overcome these deficiencies of the related art. Medical personnel would obtain a significant advantage if they could link the identity of the injured person(s) to their medical records. Because the injured person(s) may be unconscious and/or without documents, the only reliable way to identify the injured person(s) is through the use of biometrics. Biometric matching systems are not normally present in ambulances, hospitals or emergency rooms. This can result in injured person(s) being misidentified based on name or other textual data, and the record linked to the person may now contain information from someone else. Exemplary embodiments of the present invention overcome the deficiencies of the prior art with respect to difficulties in identification of injured person(s) and overcome the identified medical fraud problems, for the reasons set forth below.

SUMMARY OF THE EXEMPLARY EMBODIMENTS

A mobile System that uses biometric identification to identify an injured person(s) provides identification as well as an immediate warning of a special medical condition, and can transmit that data to the hospital along with photos and video of the injured person(s). The invention will better prepare emergency rooms with access to the patient's or injured parties medical records; the history of the patient's medical condition(s); and real-time photographs such that when the patient is brought in, the medical staff is better prepared to respond to the incoming person through medical records to identify the injured person and indicate whether the injured person has special medical conditions. The mobile medical identification and warning system includes an electronic mobile device with computational abilities including one or more of a cell phone, computer tablet, computer laptop and a portable computer system. A biometric information database of uninjured individuals containing additional identification identifiers including one or more of height, age, scar marks, other body marks, tattoos, abnormal physical attributes or other uniquely identification information of said individual is provided. A biographical information database is linked to the biometric database for identification of one or more of a name, SSN, medical record information, and other similar textual information. An alert and warning database is provided for identification of individuals with special or medical conditions including heart conditions, deafness, speech-impairment, limited vision, allergies, information relating to medicines, foods, bee stings, or other information that would be needed by the first responders. The mobile device includes an electronic biometric capture device which captures and stores data within the databases, including the photographs and videos to identify one or more facial, fingerprint, iris, etc. for collecting said biometric information from said injured person. A photographic display device on said mobile device displays the biometric and other information collected, and provides an alert in response to an individual which is identified.

Another exemplary embodiment provides a method for first responders to determine the identity of an injured individual, any special or medical conditions of the injured individual, and link said injured individual to the proper medical record; the method including the steps of selecting a database of individuals with biometric and linked biographical information; converting said biometric data into a searchable template; loading biometric matching software algorithms onto an electronic mobile device; loading said database of individuals with biometric and linked biographical information onto said electronic mobile device; loading electronic software that converts a live scan image or video taken by said mobile device into the searchable biometric template; configuring said electronic mobile device to collect live scan biometric information from said injured individual; converting said live scan biometric into the searchable template; comparing said live scan biometric from said injured individual to said database of individuals; determining whether there is a match or no-match between said injured individual and said database of individuals; displaying whether there is a match or no-match; in the case of a match, reading said biographical identification to confirm a match; in the case of a match, displaying said biographical information to confirm the match; in the case of a no-match, allowing the first responder to take another biometric for a determination of a match; and in the case of a match, transmitting the matched individual's biographical identification information to a central location that can link said injured individual's biometric to the correct medical record.

An additional exemplary embodiment provides a mobile medical identification and warning system for detecting and preventing fraudulent and illegal activities with respect to medical treatment claims and asserted medical transport of injured individuals. The system includes an electronic mobile device with computational abilities including one or more of a cell phone, a computer tablet, a computer laptop, and a portable computer system; a biometric database of biometrics or facial images of known and unknown criminals, terrorists, missing persons; uninjured individuals containing additional identification identifiers including one or more of height, age, scar marks, other body marks, tattoos, abnormal physical attributes, or other unique identification information of said individual. A biographical information database and a contextual database linked to said biometric database; an alert and warning database with law enforcement and/or military persons of interest including "bad guys," wanted persons, "be on the lookout for persons," listing possible armed, violent, "top-10," terrorist and missing persons. The mobile device includes an electronic biometric capture device which captures photographs and videos to identify one or more of facial, fingerprint, iris, etc. for collecting said biometric information from said injured person. A photographic display device on said mobile device displays the biometric collected by said biometric capture device, and provides an alert in response to an individual having special or medical information which is identified.

BRIEF DESCRIPTION OF THE SEVERAL VIEWS OF THE DRAWINGS

FIG. 3 also depicts transmission between the mobile device and the information station.

A summary of the reference numerals found in the drawings are as follows:
1. Mobile electronic device.
2. Previously collected biometric database.
3. Biographical data and text database.
4. Special or medical conditions or alerting database.
5. Biometric information collector (face, fingerprint, iris, skin, hand, or other biometric identification).
6. Mobile device display screen with a partitioned area depicting a camera photograph.
7. Mobile device display screen with a partitioned area depicting a database match screen.
8. Special or medical condition warning indicator.
9. Biometric data transmit button
10. Photographic data or video clip transmit button.
11. Information station
12. Injury photograph or video.
13. Base station or central computer.
14. Medical records database.
15. Individual medical record.
16. Electronic communications data transmission link.
17. GPS or other electronic geolocation data.
18. Date/time stamp of photo or video.
19. Mobile device identification number.
20. Additional text data.
21. Biometric database of known and unknown criminals, terrorists, etc.
22. Biographical and contextual data database.
23. Alert and warning database of terrorists, "top 10", violent, possibly armed individuals wanted by the military and or law enforcement.

DETAILED DESCRIPTION OF THE EXEMPLARY EMBODIMENTS

The figures and alternate embodiments for Method and System for a Mobile Medical Identification and Warning System are discussed below. In the exemplary embodiment illustrated in FIG. 1, a mobile device 1 with access to a biometric database 2, biographical and textual database 3 and special medical or special conditions database 4, are shown. Biometric data is collected through a biometric collector 5; facial biometric data is collected through a photograph screen 6. A match/no-match or degree of match result is then rendered on match screen 7. In the case of a no-match, the original photo can be displayed. The first responder or other person that took the photo can look at the no-match photo and determine if a good photo was taken and submitted for the match. If the person who took the photo believes that photo was poorly taken, the first responder or other person can retake the photo and resubmit the photo for matching in order to see if a match result is returned. In special cases where the face is damaged or a face photo cannot be taken, but the injured person's driver's license or ID card is available, the mobile device can attempt to make a face match from the driver's license or ID card. If the match indicates a special or medical condition exists, the warning indicator 8 will illuminate. The definition of a special or medical condition or special data includes information if the person is an organ donor, diabetic, etc.

Figure 2:
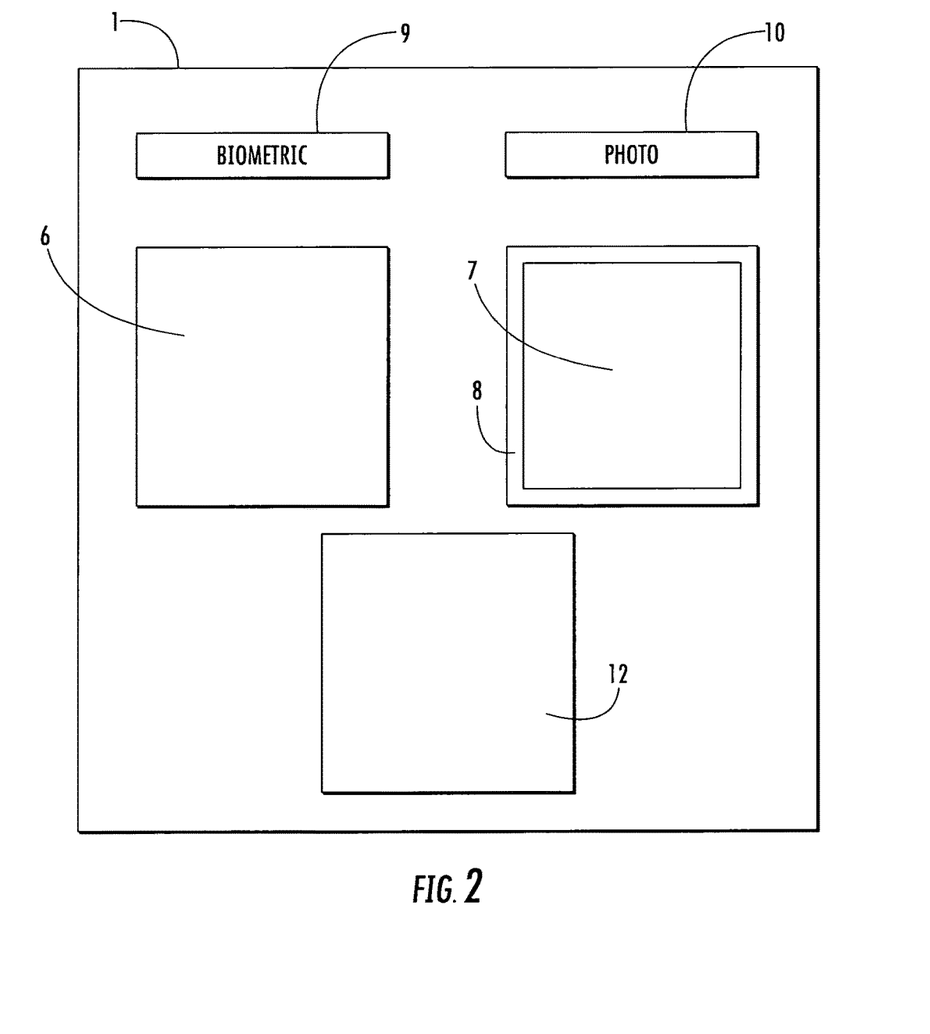
FIG. 2 depicts a front view of the mobile device, with biometric capture capability, a camera for photograph capture, a photograph screen, matching screen, and screen for capturing injury photographs or videos.

FIG. 2 depicts a biometric data transmit button 9 and photographic data transmit button 10. Biometrics data can be face, fingerprint, iris, skin, hand, or other conventional biometrics. The biometric live scan collection 6 can be transmitted to a central location such that a confirmation search and match or no-match can be made. The additional benefit of transmitting the injured person biometric and/or identity to a central medical facility is that the medial facility can retrieve the injured person's medical record and be better prepared to receive and treat the injured person(s) once they arrive. This can include contacting the injured person's regular physician for both medical records and/or special advice. Photographic data transmit button 10 can greatly assist the medical facility by sending photos or video showing the extent of injury that the injured person has received. This will assist in preparation of the emergency room with the right equipment and personnel on standby. Since the first responders and those individuals who will be assisting in treatment of the injured person(s) will be using a mobile device with communications, two way communications are possible. In addition, the photos or video can be used for medical personnel to instruct first responders to take preliminary actions to stabilize the injured person before or while the injured person(s) are being brought for treatment.

Figure 1:
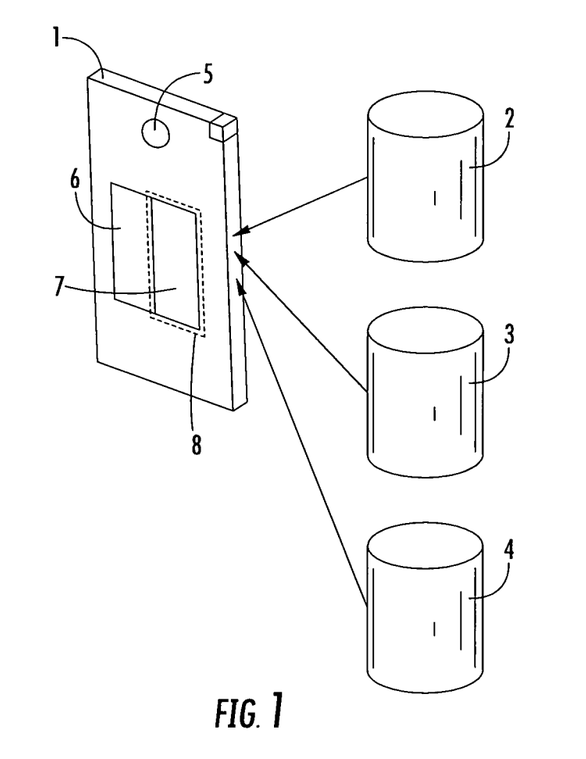
FIG. 1 depicts a perspective view of a mobile device with a biometric collection capability; a screen for capturing photographs and/or video of the injured person; a screen depicting biometric match results, and a warning indicator. The mobile device also has the capability to connect to biometric, textual and special or medical condition databases for reference purposes.
Figure 3:
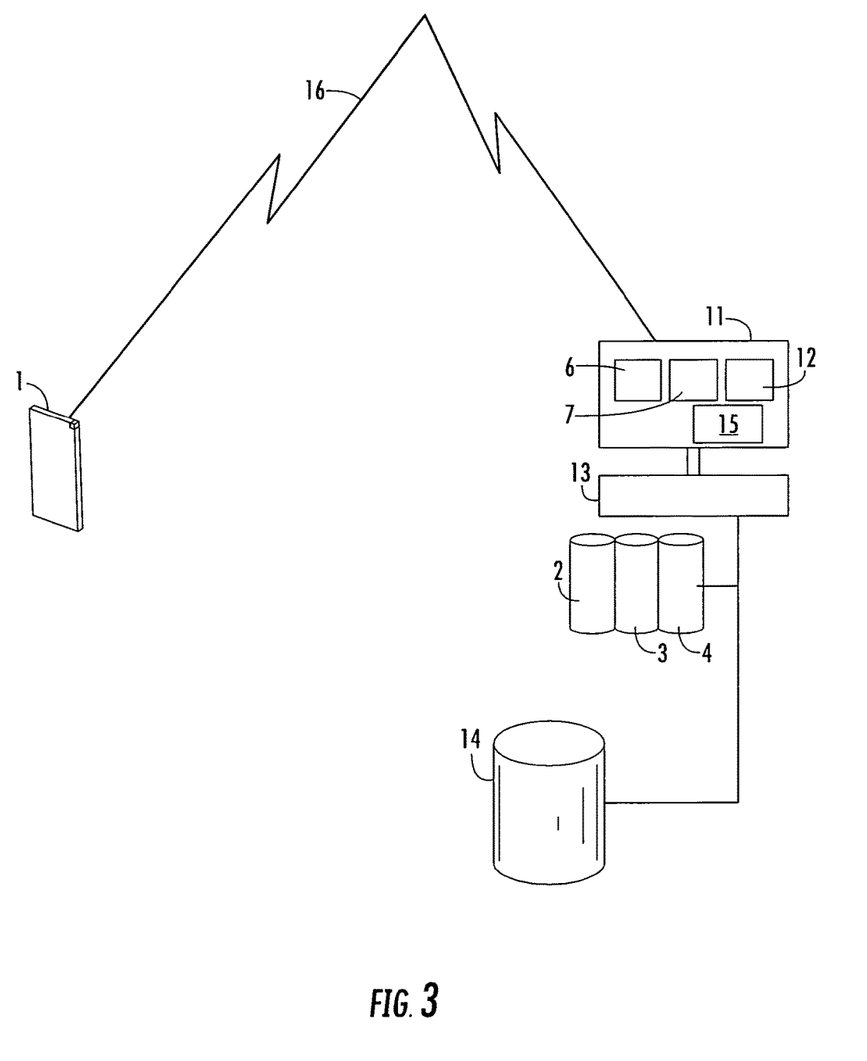
FIG. 3 depicts a perspective view of an information station with a photograph screen; a matching screen, an injury photograph/video screen, and a reference area for an individual's medical records. This station is connected to a computer, which connects to biometric, textual and special or medical condition databases. The computer also connects to a medical record database.

In the exemplary embodiment of FIG. 3, a mobile device 1, as in FIG. 1 sends data via transmission system 16 to an information station 11. The purpose and value achieved by transmitting this data 6, 7 is also discussed in the description of FIG. 2. The station includes a photograph screen 6, match screen 7, and any applicable injury photograph or video 12. The information station also includes individual medical records 15. The computer 13 provides an interface between the information station 11; the biometric database 2; the text database 3; the special or medical conditions database 4, as well as a medical records database 14.

Figure 4:
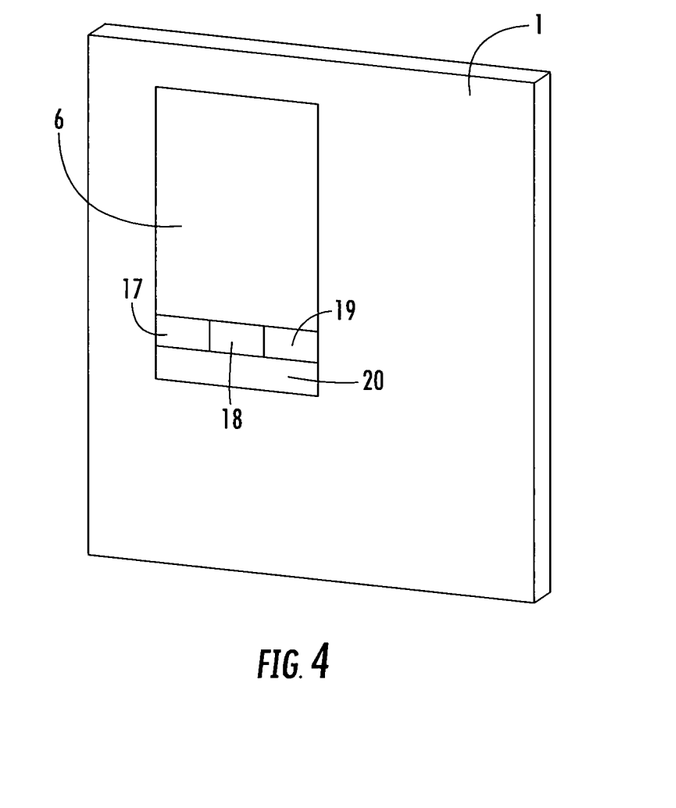
FIG. 4 depicts a perspective view of the mobile device with the photograph screen; as well as GPS location; date/time stamp; mobile device number, and additional text data.

The exemplary embodiment of FIG. 4 depicts mobile device 1 with photograph screen 6; as well as GPS location data 17; date/time stamp data 18; the mobile device 1; identification number 19, and any additional text data 20. The uses of photographic data, identity matching, geo-location, date-time stamp, and related incident photos can greatly enhance forensic investigations, claims, and legal actions at a later date.

An additional exemplary embodiment relates to reducing medical transport fraud. The mobile medical identification and warning system as described in FIGS. 1-4 can also be used to reduce a serious problem of medical transport fraud. This situation exists in environments where medical transport companies, such as ambulance drivers, are paid for each medical transportation mission they perform. For example, there is suspected $25 million dollars of ambulance driver fraud suspected in one eastern state which only has a population of one million citizens The use of the mobile medical identification and warning system with geo-location, date-time stamp, and device ID number of FIG. 4 would also serve as an excellent audit device when reviewing medical transportation billing statements. Perhaps the greatest impact would be that the knowledge and use of such a system would deter fraud in the medical transport industry, thereby reducing the cost of medical care.

Another additional exemplary embodiment relates to reducing patient identity fraud. The mobile medical identification and warning system can also be used to reduce a serious problem of medical patient identity fraud. It is estimated that 50 percent of the patient identity fraud relates to patients without medical coverage, who is "borrowing or stealing" another person's medical card and using it. The other 50 percent of patient fraud relates to a person with a medical coverage card that is willing to let someone who needs medical attention to use their medical card. In addition to the medical fraud, the more serious problem is mixing medical records, medical conditions and medical treatments. This situation can be dangerous for the person whose medical identification card and medical record is being illegally used, thereby resulting in the addition of false medical data to the medical account of the owner of the medical identification card. In addition, the person that is fraudulently using the medical identification card of another person card could also receive medical treatment that could endanger them since they are not the person they are believed to be. The use of the mobile medical identification and warning system would prevent this type of fraud and dangerous medical situation.

Yet another additional exemplary embodiment is provided for reducing physician medical claim fraud. The mobile medical identification and warning system can be used to reduce a serious problem of physician medical claim fraud. This situation is the greatest amount of medical fraud in the United States, and is estimated to amount to tens of billions of dollars annually. In this situation, a physician or medical claims organization files false medical claims relating to patients that the physician or organization did not provide treatment to, or did not administer services they claim to have provided. The mobile medical identification and warning system would track the patient through medical transport or when the patent enters the hospital. The mobile medical identification and warning system can also be used when patents walks into the hospital. The invention's identification system would positively identify the person and link them to their medical record. As the patent processes through the hospital to meet with their physician, the medical identification system could be accessed again along with the geo-location, date-time stamp, and device number. This recorded information would document that the patent was there and was seen by the doctor. This could serve as an audit review and further deter potential fraud, thus saving the healthcare system billions of dollars annually.

Figure 5:
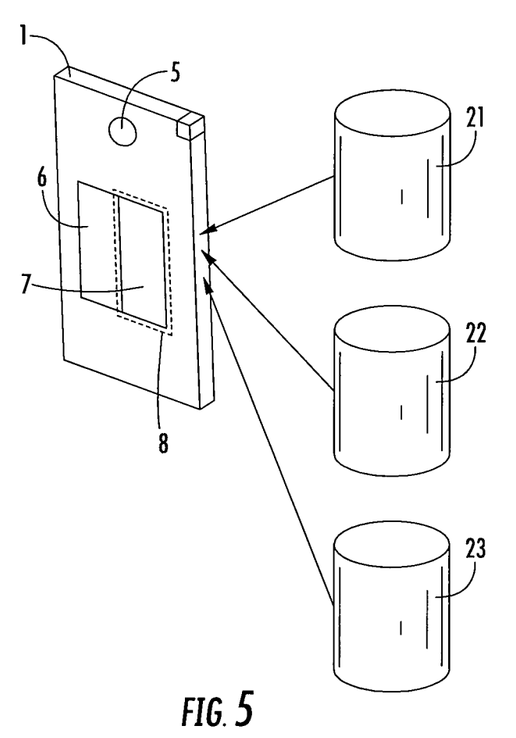
FIG. 5 is a perspective view of an exemplary embodiment for identifying individuals sought by law enforcement and the military.

A still further additional exemplary embodiment is related to Law Enforcement or Military Use. As illustrated in FIG.

5, the Mobile Medial Identification and Warning System can be simply redefined by replacing the medical data bases: (1) biometric, (2) biographical data and contextual data, (3) alert and warning data, with military or law enforcement databases for military or law enforcement persons of interest such as "bad guys," wanted persons, "be-on-the-lookout-for" persons, missing persons, etc. The medical databases discussed in the above system and method described would now engage with (A) a biometric database 21 of biometrics or facial images of known and unknown criminals, terrorists, missing persons; (B) a biographical data and contextual data database 22; and (C) an alert and warning database 23 listing possible armed, violent, "top-10," terrorist, missing person, etc. This additional exemplary embodiment replaces the three medical databases 2-4 of FIGS. 1 and 3 with the three law enforcement/military databases. The additional change is replacing transporting the injured person to a medical facility to transporting the law enforcement/military person of concern to a police station, detention facility, or interrogation facility. For the above specification and embodiments, the medical and military terms are interchangeable.

Although different embodiments of the Mobile Medical Information and Warning System have been described, it should be apparent to those skilled in the art that many more modifications besides those described therein are possible without departing from the inventive concepts herein. The inventive subject matter, therefore, is not to be restricted except in the spirit of the appended claims.

The invention claimed is:

1. A Mobile Medical Identification and Warning System for first responders to assist in identifying an injured person using links to said injured person through medical records to identify the injured person and indicating if said injured person has a special medical condition; the mobile medical identification and warning system comprising:
   a. an electronic mobile device with computational abilities including one or more of a cell phone, computer tablet, computer laptop, and a portable computer system;
   b. a biometric database of uninjured persons containing additional identification identifiers including one or more of height, age, scar marks, other body marks, tattoos, abnormal physical attributes or other uniquely identification information of said person;
   c. a biographical information database linked to said biometric database for identification of one or more of a name, social security number, medical record information and other similar textual information;
   d. an alert and warning database listing possible special or medical conditions containing medical information of said uninjured persons, including heart conditions, deafness, speech-impairment, limited vision, allergies, information relating to medicines, foods, bee stings, or other information that would be needed by the first responders;
   e. the mobile device includes an electronic biometric capture device which captures data from and stores within the databases above, including the photographs and videos to identify one or more facial, fingerprint, iris, for collecting said biometric information from said injured person; and,
   f. a photographic display device on said mobile device which displays the biometric and other collected information by said biometric capture device, and provides an alert in response if the injured person has been identified as having a special or medical condition.

2. The Mobile Medical Identification and Warning System of claim 1, wherein the biometric that is used in the reference biometric database by the first responders' live scan device is the facial biometric.

3. The Mobile Medical Identification and Warning System of claim 1, wherein the biometric that is used in the reference biometric database by the first responders' live scan device is the fingerprint biometric.

4. The Mobile Medical Identification and Warning System of claim 1, wherein the biometric that is used in the reference biometric database by the first responders' live scan device is the iris biometric.

5. The Mobile Medical Identification and Warning System of claim 1, wherein the biometric capture device includes a transmit button which transmits the biometric obtained by a first responder to a central location.

6. The Mobile Medical Identification and Warning System of claim 1, wherein the photographic display device includes a photograph or video transmit button which transmits the photograph or video of the injured person to a central location.

7. The Mobile Medical Identification and Warning System of claim 1, further including a GPS location determining device to identify and save the GPS location of the injured person.

8. The Mobile Medical Identification and Warning System of claim 1, wherein the mobile device further includes a device for determining the date and time of the use of the system and which transfers to a central location the date and time information along with the rest of the collected information related to the injured person.

9. The Mobile Medical Identification and Warning System of claim 1, wherein the system includes a device identification number.

10. A method for first responders to determine the identity of an injured person, any special or medical conditions of the injured person, and link said injured person to the proper medical record, the method comprising the steps of:
   a. selecting a database of persons with biometric and linked biographical information;
   b. converting said biometric data into a searchable template;
   c. loading biometric matching software algorithms onto an electronic mobile device;
   d. loading said database of persons with biometric and linked biographical information onto said electronic mobile device;
   e. loading electronic software that converts a live scan image or video taken by said mobile device into a searchable biometric template;
   f. configuring said electronic mobile device to collect live scan biometric information from said injured person;
   g. converting said live scan biometric into a searchable template;
   h. comparing said live scan biometric from said injured person to said database of persons;
   i. determining whether there is a match or no-match between said injured person and said database of persons;
   j. displaying whether there is a match or no-match;
   k. in the case of a match, reading said biographical identification to confirm a match;
   l. in the case of a match, displaying said biographical information to confirm the match;
   m. in the case of a no-match, allowing the first responder to take another biometric for a determination of a match; and n. in the case of a match, transmitting the matched person's biographical identification information to a central location that can link said injured person's biometric to the correct medical record.

11. A method for first responders to determine the identity of an injured person of claim 10, further comprising the step of the central location retrieving said injured person's medical record based on said person's biographical identification information transmitted to the central location.

12. The method for first responders to determine the identity of an injured person of claim 11, wherein the central location is selected from a group of hospitals, emergency reaction centers, or medical centers.

13. The method for first responders to determine the identity of an injured person of claim 12, further comprising the step of recording a live scan of the GPS location of the injured person.

14. The method for first responders to determine the identity of an injured person of claim 10, further comprising the step of recording of the date/time stamp of the live scan image or video of the injured person.

15. The method for first responders to determine the identity of an injured person of claim 10, further comprising the step of recording of the mobile device identification number as a reference identification of who collected the data.

16. The method for first responders to determine the identity of an injured person of claim 10, further comprising the step of filing a video of the injured person.

17. The method for first responders to determine the identity of an injured person of claim 10, further comprising the step of filing photographs of the injured person.

18. The method for first responders to determine the identity of an injured person of claim 10, further comprising the step of filing photographs or videos for evidentiary purposes.

19. The method for first responders to determine the identity of an injured person of claim 10, further comprising the step of matching the person's medical record against records at a central location.

20. A Mobile Medical Identification and Warning System for detecting and preventing fraudulent and illegal activities with respect to medical treatment claims and asserted medical transport of injured persons, the mobile medical identification and warning system comprising:

a. an electronic mobile device with computational abilities including one or more of a cell phone, a computer tablet, a computer laptop, and a portable computer system;

b. a biometric database of biometrics or facial images of known and unknown criminals, terrorists and missing persons;

c. a biographical information database and a contextual database linked to said biometric database;

d. an alert and warning database with law enforcement and/or military persons of interest including "bad guys," wanted persons, "be on the lookout for persons," listing possible armed, violent, "top-10," terrorist and missing persons;

e. the mobile device includes an electronic biometric capture device which captures photographs and videos to identify one or more of facial, fingerprint, iris, for collecting said biometric information from said injured person; and, f. a photographic display device on said mobile device which displays the biometric collected by said biometric capture device; and g. transferring the collected information relating to the law enforcement/military person of concern to a police station, detention facility or interrogation facility.

* * * * *